(12) United States Patent
Dubois

(10) Patent No.: US 8,440,859 B2
(45) Date of Patent: May 14, 2013

(54) METHOD FOR PRODUCING BIORESOURCED PROPIONIC ACID FROM GLYCEROL

(75) Inventor: Jean-Luc Dubois, Millery (FR)

(73) Assignee: Arkema France, Colombes (FR)

( * ) Notice: Subject to any disclaimer, the term of this patent is extended or adjusted under 35 U.S.C. 154(b) by 217 days.

(21) Appl. No.: 13/055,263

(22) PCT Filed: Jul. 22, 2009

(86) PCT No.: PCT/FR2009/051470
§ 371 (c)(1), (2), (4) Date: Jan. 21, 2011

(87) PCT Pub. No.: WO2010/010298
PCT Pub. Date: Jan. 28, 2010

(65) Prior Publication Data
US 2011/0124913 A1    May 26, 2011

(30) Foreign Application Priority Data
Jul. 22, 2008  (FR) ...................... 08 54976

(51) Int. Cl.
C07B 53/00   (2006.01)
(52) U.S. Cl.
USPC ....................................... 562/606
(58) Field of Classification Search .............. None
See application file for complete search history.

(56) References Cited

U.S. PATENT DOCUMENTS

| | | | |
|---|---|---|---|
| 3,689,541 A | 9/1972 | Sennewald et al. | |
| 3,798,264 A | 3/1974 | Kubota et al. | |
| 3,932,500 A | 1/1976 | Doembgen et al. | |
| 4,039,428 A * | 8/1977 | Wei ................. | 203/37 |
| 4,493,719 A | 1/1985 | Wintermantel et al. | |
| 5,387,720 A | 2/1995 | Neher et al. | |
| 5,426,221 A | 6/1995 | Willersinn | |
| 5,504,247 A | 4/1996 | Saxer et al. | |
| 5,780,679 A | 7/1998 | Egly et al. | |
| 5,831,124 A | 11/1998 | Machhammer et al. | |
| 6,281,386 B1 | 8/2001 | Fauconet et al. | |
| 6,482,981 B2 | 11/2002 | Ueno et al. | |
| 7,612,230 B2 | 11/2009 | Shima et al. | |
| 2009/0065400 A1 | 3/2009 | Song et al. | |
| 2009/0068440 A1 | 3/2009 | Bub et al. | |
| 2009/0134357 A1 | 5/2009 | Bub et al. | |
| 2010/0168471 A1 | 7/2010 | Dubois | |

FOREIGN PATENT DOCUMENTS

| | | |
|---|---|---|
| DE | 4308087 A1 | 9/1994 |
| DE | 10225339 | 3/2002 |
| EP | 0706986 A1 | 4/1996 |
| EP | 1710227 A1 | 10/2006 |
| FR | 2756280 | 5/1998 |
| GB | 1416286 | 12/1975 |
| JP | 03-181440 | 7/1991 |
| WO | 2006/087083 A2 | 8/2006 |
| WO | 2006/092272 A2 | 9/2006 |
| WO | 2006/114506 A1 | 11/2006 |
| WO | 2006/136336 A2 | 12/2006 |
| WO | 2008/087315 A2 | 4/2008 |

OTHER PUBLICATIONS

Suwannakham et al., (2005) Biotechnol. Bioeng. 91:325-337.*
Ballerini, D. et al., "Methanolyse des huiles vegetales", l'Actualite Chemique, Nov.-Dec. 2009.
Tanabe, K., et al. "Studies in Surface Science and Catalysis, New Solid Acids and Bases", vol. 51, 1989, pp. 1-25.
Byrne, M. et al. "The Cathodic Reduction of Acrylic Acid on Platinum, Electrochemical Chemistry and Interfacial Electrochemistry", 60, (1975), pp. 75-80.

* cited by examiner

*Primary Examiner* — Karl J Puttlitz
(74) *Attorney, Agent, or Firm* — Buchanan Ingersoll & Rooney

(57) ABSTRACT

The invention relates to a method for producing bioresourced propionic acid from glycerol. The invention also relates to a composition comprising more than 85 mass % of bioresourced propionic acid, and to the use of the propionic acid obtained from the method as a solvent, as a food preservative, for producing herbicide or for preparing vinyl propionate.

9 Claims, No Drawings

METHOD FOR PRODUCING BIORESOURCED PROPIONIC ACID FROM GLYCEROL

FIELD OF THE INVENTION

The present invention is targeted at a process for the manufacture of bioresourced propionic acid from glycerol as starting material, the term "bioresourced acid" indicating that the propionic acid is essentially obtained from a carbon source of renewable origin.

BACKGROUND OF THE INVENTION

Propionic acid is a material which can be used as solvent, as food preservative or in the herbicide manufacture; propionic acid also participates in the preparation of vinyl propionate, which is used as monomer in (co)polymers with, for example, ethylene, vinyl chloride or (meth)acrylic esters.

Processes for the synthesis of propionic acid are known in the prior art. For example, patent application DE 102 25 339 A1 describes a process for the preparation of propionic acid by catalytic hydrogenation of acrylic acid in the presence of molecular oxygen and of a catalyst of an element from groups 8 to 11. Conventionally, acrylic acid is obtained by catalytic gas-phase oxidation of propane, propylene and/or acrolein.

One of the problems posed by the processes for the synthesis of propionic acid of the prior art is that they are carried out starting from nonrenewable starting materials of fossil (oil) origin, in particular propane or propylene. In point of fact, resources of these starting materials are limited and the extraction of oil requires drilling at increasingly deep depths and under technical conditions which are always more difficult, requiring sophisticated equipment and the use of processes which are always more expensive in energy. These constraints have a direct consequence with regard to the cost of manufacturing propionic acid.

Furthermore, manufacturers for some years have directed their research and development studies at "bioresourced" processes of synthesis using renewable natural starting materials.

For example, for the manufacture of acrylic acid resulting from renewable resources, alternative processes have recently been developed starting from nonfossil plant starting materials. In particular, processes starting from glycerol (also known as glycerin), resulting from the methanolysis of fatty substances, have been developed. This glycerol is available in large amounts and can be stored and transported without difficulty.

The methanolysis of vegetable oils or animal fats can be carried out according to various well known processes, in particular by using homogeneous catalysis, such as sodium hydroxide or sodium methoxide in solution in methanol, or by using heterogeneous catalysis. Reference may be made, on this subject, to the paper by D. Ballerini et al. in l'Actualité Chimique of November-December 2002.

As regards the conversion of glycerol by the chemical route, mention may be made of the synthesis of acrylic acid in two stages, namely the production of acrolein by dehydration of glycerol, which is described in particular in patent U.S. Pat. No. 5,387,720, followed by a "conventional" oxidation of the acrolein to produce acrylic acid.

The first stage in the manufacture of acrylic acid from glycerol results in the same intermediate compound as the conventional manufacturing process starting from propylene, namely acrolein, according to the reaction:

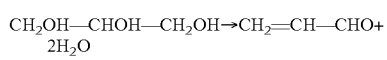

which is followed by the second oxidation stage according to the reaction

Patent applications EP 1 710 227, WO2006/136336 and WO2006/092272 describe such processes for the synthesis of acrylic acid from glycerol comprising the stage of gas-phase dehydration in the presence of catalysts consisting of inorganic oxides (mixed or unmixed) based on aluminum, titanium, zirconium, vanadium, and the like, and the stage of gas-phase oxidation of the acrolein thus synthesized in the presence of catalysts based on oxides of iron, molybdenum, copper, and the like, alone or in combination in the form of mixed oxides.

However, one of the problems posed by these processes is that the acrylic acid is not the only product formed and that by-products are formed in large amounts, such as propionic acid and impurities, such as water, acrylic acid dimers, acetic acid, acrolein, benzaldehyde, furfurals or hydroquinone. It is thus generally necessary to purify the acrylic acid by conventional techniques in order to obtain a more concentrated acrylic acid solution.

As the quality of the acrylic acid, that is to say its content of various impurities, plays a large role in the subsequent polymerization processes, manufacturers manufacturing this acrylic acid have been led to bring into play a whole series of purification stages in order to obtain a "standard" acrylic acid, which is normally referred to as glacial acrylic acid (gAA). This gAA does not meet officially recognized specifications having a universal nature but means, for its manufacturer, the level of purity to be achieved in order to be able to successfully carry out its subsequent conversions. By way of example, for an acrylic acid resulting from propylene, the reactor outlet stream is subjected to a combination of stages which can differ in their sequence depending on the process: removal of the noncondensable products and of the bulk of the very light compounds, in particular the intermediate acrolein in the synthesis of the acrylic acid (crude AA), dehydration removing the water and the formaldehyde (dehydrated AA), removal of the light products (in particular the acetic acid), the removal of the heavy products, optionally removal of certain residual impurities by chemical treatment.

This process is highly analogous to the process for synthesis from propylene in so far as the intermediate product, the acrolein, resulting from the first stage is the same and as the second stage is carried out under the same operating conditions. However, the first-stage reaction of the process of the invention, dehydration reaction, is different from the propylene oxidation reaction of the normal process. The dehydration reaction, carried out in the gas phase, is carried out using solid catalysts different from those used for the oxidation of propylene. The aerolein-rich stream resulting from the first dehydration stage, intended to feed the second stage of oxidation in the acrolein to give acrylic acid, comprises a greater amount of water and in addition exhibits substantial differences as regards by-products resulting from the reaction mechanisms involved being given material formed by the different selectivities in each of the two routes.

In order to illustrate these differences, the data relating to the presence of various acids in the crude acrylic acid, that is to say in the liquid phase exiting from the reactor of the second stage according to the state of the art, are collated in table 1 below.

TABLE 1

| Impurity/AA (crude acrylic acid) ratio by weight | Ex-propylene process | Ex-glycerol process |
|---|---|---|
| Acetic acid/AA | <5% | >10% |
| Propionic acid/AA | <0.1% | >0.5% |

Some of the main differences, in terms of constituents of the liquid stream exiting from the oxidation reactor, between the ex-propylene and ex-glycerol processes are illustrated in table 1. Naturally, although this is not mentioned in the table, a whole series of oxygen-comprising compounds, alcohols, aldehydes, ketones and other acids, the necessary separation of which is known to a person skilled in the art, is also found in the crude acrylic acid, whether it originates from the ex-propylene process or from the ex-glycerol process.

The acetic acid and the propionic acid cause difficulties for the acrylic acid, in particular because they are not converted during the polymerization process; they are saturated and thus cannot be polymerized. Depending on the polymerization process involved and the applications targeted for the polymer, these impurities may remain in the finished product and risk conferring undesirable corrosive properties on the finished product or be reencountered in the liquid or gaseous discharges generated by the polymerization process and cause organic pollution, which is also undesirable. They therefore have to be removed.

The acetic acid can be removed by distillation in a light fraction, an operation generally denoted topping. However, the reduction in the concentration of acetic acid in the context of the ex-glycerol process results in a consequent loss of acrylic acid in the light fraction, as a result, on the one hand, of the large difference existing between its initial content in the crude acrylic acid and its targeted content in the technical acrylic acid and, on the other hand, of the existence of hydrogen bonds existing between the carboxyl groups of the two molecules. This disadvantage is important economically as the production of a glacial acrylic acid with an acetic acid content of less than 0.1% by weight can only be carried out at the expense of the degree of recovery of the acrylic acid exiting from the oxidation reactor.

As regards the propionic acid, the extremely small difference in volatility existing between this impurity to be removed and the acrylic acid to be purified (of the order of 1° C.) prevents any purification of the acrylic acid by distillation under economically acceptable conditions.

There exists, in the prior art, no process which makes possible the manufacture of compositions sufficiently concentrated in propionic acid of renewable origin to allow them to be used in the conventional applications of the propionic acid obtained with fossil starting materials.

DETAILED DESCRIPTION OF THE INVENTION

Advantageously and surprisingly, the Company applying for the present patent application has employed a process for the industrial manufacture of propionic acid from glycerol.

The process according to the invention makes it possible to dispense at least in part with starting materials of fossil origin and to replace them with renewable starting materials.

The propionic acid obtained according to the process according to the invention has a quality such that it can be used in all applications in which it is known to use propionic acid, including in applications with the highest standards.

A subject matter of the invention is a process for the manufacture of bioresourced propionic acid from glycerol comprising the following stages:

gas-phase catalytic dehydration of the glycerol to give acrolein, (I)

partial condensation by cooling and extraction of a portion of the water present in the reaction medium from (1), (1')

gas-phase catalytic oxidation of the acrolein to give acrylic acid, (2)

extraction of the acrylic acid present in the stream from the oxidation by absorption with a solvent, (3)

drying the acrylic acid solution by distillation in the presence of a water-immiscible solvent, (4)

distillation of the solution thus obtained in order to remove the light compounds (topping), (5)

distillation of the heavy fraction resulting from the preceding stage (5) in order to remove the heavy compounds (tailing), (6)

combined with a stage of extraction of the acrylic acid by fractional crystallization applied to one of the following streams: the heavy fraction from (4), heavy fraction from (5) or light fraction from (6), in order to isolate crystals of purified acrylic acid and a solution of mother liquors depleted in acrylic acid catalytic hydrogenation of the mother liquors isolated in the fractional crystallization stage in the presence of molecular hydrogen in order to form a propionic acid solution separation of the propionic acid, for example by distillation.

The process according to the invention makes it possible to obtain a bioresourced propionic acid obtained from renewable resources.

A renewable starting material is a natural resource, the stock of which can be reconstituted over a short period on the human scale. In particular, it is necessary for the stock to be able to be renewed as quickly as it is consumed. For example, plant materials exhibit the advantage of being able to be cultivated without their consumption resulting in an apparent reduction in natural resources.

Unlike the materials resulting from fossil materials, renewable starting materials comprise $^{14}C$. All the samples of carbon drawn from living organisms (animals or plants) are in fact a mixture of 3 isotopes: $^{12}C$ (representing approximately 98.892%), $^{13}C$ (approximately 1.108%) and $^{14}C$ (traces: $1.2 \times 10^{-10}$%). The $^{14}C/^{12}C$ ratio of living tissues is identical to that of the atmosphere. In the environment, $^{14}C$ exists in two predominant forms: in the form of carbon dioxide gas ($CO_2$) and in the organic form, that is to say in the form of carbon incorporated in organic molecules.

In a living organism, the $^{14}C/^{12}C$ ratio is kept constant metabolically as the carbon is continually exchanged with the external environment. As the proportion of $^{14}C$ is constant in the atmosphere, it is the same in the organism, as long as it is living, since it absorbs this $^{14}C$ in the same way as the surrounding $^{12}C$. The mean $^{14}C/^{12}C$ ratio is equal to $1.2 \times 10^{-12}$.

$^{12}C$ is stable, that is to say that the number of $^{12}C$ atoms in a given sample is constant over time. $^{14}C$ is radioactive and the number of $^{14}C$ atoms in a sample decreases over time (t), its half-life being equal to 5730 years.

The $^{14}C$ content is substantially constant from the extraction of the renewable starting materials up to the manufacture of the bioresourced propionic acid and even up to the end of the use of the object comprising propionic acid.

Consequently, the presence of $^{14}C$ in a material, this being the case whatever the amount thereof, gives an indication with regard to the origin of the molecules constituting it, namely that they originate from renewable starting materials and not from fossil materials.

The amount of $^{14}C$ in a material can be determined by one of the methods described in the standard ASTM D6866-06 (Standard Test Methods for Determining the Biobased Content of Natural Range Materials Using Radiocarbon and Isotope Ratio Mass Spectrometry Analysis).

This standard comprises three methods for measuring organic carbon resulting from renewable starting materials, known as biobased carbon. The proportions shown for the propionic acid of the invention are preferably measured according to the mass spectrometry method or the liquid scintillation spectrometry method described in this standard and very preferably by mass spectrometry.

These measurement methods evaluate the ratio of the $^{14}C/^{12}C$ isotopes in the sample and compare it with a ratio of the $^{14}C/^{12}C$ isotopes in a material of biological origin giving the 100% standard, in order to measure the percentage of organic carbon in the sample.

Preferably, the propionic acid according to the invention comprises an amount of carbon resulting from renewable starting materials of greater than 20% by weight, preferably greater than 40% by weight, with respect to the total weight of carbon of the propionic acid.

In other words, the propionic acid can comprise at least $0.25\times10^{-10}\%$ by weight of $^{14}C$ and preferably at least $0.5\times10^{-10}\%$ by weight of $^{14}C$.

Advantageously, the amount of carbon resulting from renewable starting materials is greater than 75% by weight, preferably equal to 100% by weight, with respect to the total weight of carbon of the propionic acid.

According to the process of the invention, the acrylic acid is purified by fractional crystallization. During this purification, two streams are obtained: a first stream concentrated in acrylic acid, which can be recovered in value as acrylic acid, and a second stream (mother liquors) poorer in acrylic acid. This second stream cannot be recovered in value as acrylic acid. According to the process of the invention, this second stream is hydrogenated to form bioresourced propionic acid. The manufacturing process according to the invention makes it possible to obtain a purified acrylic acid and to recover in value the second stream and thus delimit the losses of product during the process.

For the implementation of the process, use is generally made of a stream feeding the reactor of the stage (1) comprising the glycerol and water, with a water/glycerol ratio by weight which can vary within wide limits, for example between 0.04/1 and 9/1 and preferably between 0.7/1 and 3/1. The dehydration reaction, stage (1), which is an equilibrium reaction but one favored by a high temperature level, is generally carried out in the gas phase in the reactor in the presence of a catalyst at a temperature ranging from 150° C. to 500° C., preferably of between 250° C. and 350° C., and an absolute pressure of between 1 and 5 bar (1000 and 5000 kPa). It can also be carried out in the presence of oxygen or of a gas comprising oxygen, as described in applications WO 06/087083 and WO 06/114506.

The glycerol dehydration reaction is generally carried out over solid acid catalysts. The catalysts which are suitable are materials used in a gaseous or liquid reaction medium, in a heterogeneous phase, which have a Hammett acidity, denoted $H_0$, of less than +2. As indicated in patent U.S. Pat. No. 5,387,720, which refers to the paper by K. Tanabe et al. in "Studies in Surface Science and Catalysis", Vol. 51, 1989, chap. 1 and 2, the Hammett acidity is determined by amine titration using indicators or by adsorption of a base in the gas phase.

These catalysts can be chosen from natural or synthetic siliceous substances or acidic zeolites; inorganic supports, such as oxides, covered with mono-, di-, tri- or polyacidic inorganic acids; oxides or mixed oxides or heteropolyacids or heteropolyacid salts.

These catalysts can generally consist of a heteropolyacid salt in which the protons of said heteropolyacid are exchanged with at least one cation chosen from elements belonging to Groups I to XVI of the Periodic Table of the Elements, these heteropolyacid salts comprising at least one element chosen from the group consisting of W, Mo and V.

Mention may particularly be made, among mixed oxides, of those based on iron and on phosphorus and of those based on cesium, phosphorus and tungsten.

The catalysts are chosen in particular from zeolites, Nafion® composites (based on sulfonic acid of fluoropolymers), chlorinated aluminas, phosphotungstic and/or silicotungstic acids and acid salts, and various solids of the type comprising metal oxides, such as tantalum oxide $Ta_2O_5$, niobium oxide $Nb_2O_5$, alumina $Al_2O_3$, titanium oxide $TiO_2$, zirconia $ZrO_2$, tin oxide $SnO_2$, silica $SiO_2$ or silicoaluminate $SiO_2/Al_2O_3$, impregnated with acid functional groups, such as borate $BO_3$, sulfate $SO_4$, tungstate $WO_3$, phosphate $PO_4$, silicate $SiO_2$ or molybdate $MoO_3$ functional groups, or a mixture of these compounds.

The preceding catalysts can additionally comprise a promoter, such as Au, Ag, Cu, Pt, Rh, Pd, Ru, Sm, Ce, Yt, Sc, La, Zn, Mg, Fe, Co, Ni or montmorillonite.

The preferred catalysts are phosphated zirconias, tungstated zirconias, silica zirconias, titanium or tin oxides impregnated with tungstate or phosphotungstate, phosphated aluminas or silicas, heteropolyacids or heteropolyacid salts, iron phosphates and iron phosphates comprising a promoter.

The reaction medium exiting from the dehydration reactor has a high water content due to the glycerol charge (aqueous solution) and to the reaction itself. An additional stage (1') of partial condensation of the water, such as, for example, that described in the patent application WO 08/087315 on behalf of the Applicant Company, will make it possible to remove a portion thereof, so as to bring this gas to a composition substantially identical to that of the ex-propylene process, in order to feed the second stage of oxidation of the acrolein to give acrylic acid. The term "substantially identical composition" is understood to mean in particular similar concentrations of acrolein, water and oxygen. This condensation stage (1') can be carried out with cooling to a temperature which makes it possible to obtain, after removal of the condensed phase, a gas stream comprising water and acrolein in a water/acrolein molar ratio of 1.5/1 to 7/1. This partial condensation of the water makes it possible to prevent damage to the catalyst of the 2nd stage of oxidation of the acrolein to give acrylic acid and to avoid, during the subsequent stages, the removal of large amounts of water, which is expensive and which risks bringing about losses of acrylic acid. In addition, it makes it possible to remove a portion of the "heavy" impurities formed during the dehydration.

The oxidation reaction, stage (2), is carried out in the presence of molecular oxygen or of a mixture comprising molecular oxygen at a temperature ranging from 200° C. to 350° C., preferably from 250° C. to 320° C., and under a pressure ranging from 1 to 5 bar in the presence of an oxidation catalyst.

Use is made, as oxidation catalyst, of any type of catalyst well known to a person skilled in the art for this reaction. Use is generally made of solids comprising at least one element chosen from the list Mo, V, W, Re, Cr, Mn, Fe, Co, Ni, Cu, Zn, Sn, Te, Sb, Bi, Pt, Pd, Ru and Rh, present in the metallic form or in the oxide, sulfate or phosphate form. Use is made in particular of the formulations comprising Mo and/or V and/or W and/or Cu and/or Sb and/or Fe as main constituents.

The gas mixture resulting from stage (2) is composed, apart from the acrylic acid:
- of light compounds which are noncondensable under the temperature and pressure conditions normally employed: nitrogen, unconverted oxygen, carbon monoxide and carbon dioxide, which are formed in a small amount by final oxidation,
- of condensable light compounds: in particular water, generated by the dehydration reaction or present as diluent, unconverted acrolein, light aldehydes, such as formaldehyde and acetaldehyde, formic acid, acetic acid and propionic acid,
- of heavy compounds: furfuraldehyde, benzaldehyde, maleic acid, maleic anhydride, 2-butenoic acid, benzoic acid, phenol, protoanemonin, and the like.

Stage (3) consists of an extraction of the acrylic acid by absorption in a solvent. The solvent can be water or a mixture of heavy hydrophobic solvents, such as diphenyl and diphenyl ether. This extraction stage is known to a person skilled in the art and the latter may refer to the following patents: French patent No. 1 588 432, French patent No. 2 146 386, German patent No. 4 308 087, European patent No. 0 706 986 and French patent No. 2 756 280. This extraction can be carried out with water by a countercurrentwise absorption. For this, the gas resulting from the reactor is introduced at the bottom of an absorption column, where it encounters, countercurrentwise, water introduced at the column top. Light compounds (mainly acetaldehyde and acrolein) are essentially removed at the top of this absorption column. The water used as absorbing solvent can be introduced via a source external to the process but will preferably be composed, partially or completely, by recovery from at least one of the gaseous reaction streams resulting from the initial reaction stages, for example the water resulting from stages (1') and (4), namely the water condensed in stage 1' or the water recovered from the azeotropic drying column top stream. The operating conditions of this absorption stage are as follows: The gaseous reaction mixture is introduced at the column bottom at a temperature between 130° C. and 250° C. The water is introduced at the column top at a temperature of between 10° C. and 60° C. The respective amounts of water and of gaseous reaction mixture are such that the water/acrylic acid ratio by weight is between 1/1 and 1/4. The operation is carried out at atmospheric pressure.

In a preferred alternative embodiment of the process, during a stage (3'), the acrolein present in the liquid fraction resulting from (3) is recovered by distillation or stripping with a gas. In this alternative form of the process, the absorption column can be coupled to a column for the distillation of the very light compounds, essentially acrolein unconverted on conclusion of reaction, present in a low concentration in the aqueous acrylic acid solution recovered at the bottom of the absorption column. This distillation column, which operates under a pressure of from $6 \times 10^3$ to $7 \times 10^4$ Pa, is fed at the top with the bottom stream from the preceding absorption column and makes it possible to remove, at the top, a stream of acrylic acid enriched in acrolein which is recycled in the lower part of the absorption column (3) for final removal at the top of this same column. An aqueous mixture of acrylic acid in water (ratio by weight from 1/1 to 4/1) is thus obtained which is freed from the bulk of the unconverted acrolein, which aqueous mixture is known as "crude acrylic acid". The acrolein can also be recovered by stripping with a gas, such as air or an inert gas mixture preferably comprising oxygen.

This stage is optional but, in its absence, the crude acrylic acid will be more concentrated in acrolein, which will have to be removed during the subsequent topping stage. Furthermore, this stage (3') makes it possible to recover and recycle the acrolein to the reaction stage (2) and thus to increase the overall yield of the process.

Stage (4) is a dehydration or drying stage which is carried out in the presence of a water-immiscible solvent for acrylic acid. This dehydration stage can be carried out by liquid/liquid extraction of the acrylic acid in the presence of the solvent, followed by a stage of separation of the monomer, acrylic acid, by distillation.

This dehydration stage is described in numerous patents; see, for example, patent FR 2 119 764, with methyl isobutyl ketone (MIBK) as solvent, or patent U.S. Pat. No. 3,689,541, with trimethylcyclohexanone as solvent, or by distillation in the presence of a solvent or of mixtures of solvents forming a heterogeneous azeotrope with the water, such as acetates or methyl isobutyl ketone, such as described, for example, in patent FR 2 554 809, or solvents additionally forming an azeotropic mixture with acetic acid, such as toluene, as described, for example, in the patent JP 03.181.440.

In the process of the invention, use will preferably be made, for this dehydration stage, of an azeotropic distillation using a solvent, such as MIBK. The distillation column, which operates under a pressure of from $6 \times 10^3$ to $7 \times 10^4$ Pa, is equipped with a decanter which receives the column top stream after condensation and provides for the separation of an upper organic phase, essentially consisting of MIBK, which is completely recycled as column top reflux, and of an aqueous phase comprising the water and most of the formaldehyde. The heating power set for the boiler of the column is adjusted such as to obtain a solvent reflux flow rate such that the ratio by weight of solvent returned as reflux to water present in the crude acrylic acid feeding the column corresponds to the theoretical azeotropic mixture. The stream obtained at the column bottom, the dehydrated acrylic acid, is essentially devoid of water (generally less than 1% by weight).

In an alternative embodiment, this column can be coupled to a second column for recovery of the solvent, so as to recover, in the aqueous stream separated by settling at the top of the azeotropic distillation column, the traces of solvent dissolved in the aqueous phase. These small amounts of solvent, distilled and condensed at the top of this solvent recovery column, which operates at atmospheric pressure, are subsequently recycled in the decanter of the preceding column. The aqueous stream from the bottom of this solvent recovery column is discarded.

Stage (5) is a stage of removal of the light compounds, in particular acetic acid and formic acid, by distillation; it is generally known as "topping". The stream of dehydrated acrylic acid obtained at the bottom of the azeotropic distillation column is conveyed to the middle part of a distillation column which operates under a top pressure of the order of $2 \times 10^3$ to $2 \times 10^4$ Pa. The stream from the column bottom comprises acrylic acid freed from the bulk of the light compounds. The column top stream, which is rich in acetic acid and formic acid, can optionally be additionally treated in order to recover, in a second column in series, the small amounts of acrylic acid entrained with the column top stream.

Stage (6) is a stage of separation of the heavy compounds by distillation. The bottom stream from the preceding topping column is introduced at the bottom of a distillation column operating under a top pressure of the order of $2 \times 10^3$ to $2 \times 10^4$ Pa. A stream of purified acrylic acid described as of technical grade is obtained at the top.

The various stages of separating by distillation necessitate, due to the thermodynamic conditions employed, the addition of polymerization inhibitors to the streams treated in order to prevent the formation of heavy compounds formed by polymerization of acrylic acid which are harmful to the satisfactory operation of the assembly. The polymerization inhibitors generally used for the stages of purification of the acrylic acid are phenolic products, such as hydroquinone or hydroquinone methyl ether, phenothiazine derivatives, compounds of the family of the thiocarbamates, such as copper di(n-butyl)dithiocarbamate, amino derivatives, such as hydroxylamines, hydroxydiphenylamine or derivatives of the family of the phenylenediamines, nitroxide derivatives of 4-hydroxy 2,2,6,6-tetramethylpiperidine-1-oxyl (TEMPO), such as 4-hydroxy-TEMPO or 4-oxo-TEMPO, or metal salts, such as manganese acetate. These inhibitors can be used alone or in combination and are in addition preferably introduced in combination with an oxygen-comprising gas.

These polymerization inhibitors are generally heavy compounds, the volatility of which is lower than that of acrylic acid. They are removed at the bottom of the columns. On the other hand, their concentration in the vapor phase inside the distillation columns is low and insufficient to prevent the initiation of polymers. In order to prevent the appearance and the accumulation of polymers, these additives are usually introduced into the liquid streams feeding the devices, but also at the top and at various points of the columns and devices, so as to provide continuous and homogeneous reflux of solution rich in polymerization inhibitors over all the parts of the devices. Generally, they are conveyed in solution in a liquid, for example in acrylic acid or in water, if the purification stage relates to aqueous streams.

The process of the invention comprises a stage of purification of the bioresourced acrylic acid which is a separation by fractional crystallization.

Fractional crystallization is a well known separation technique. It can be carried out in various forms, dynamic crystallization, static crystallization or suspension crystallization. Mention may be made, on this subject, of the French patent 77 04510 of Feb. 17, 1977 (BASF) and the U.S. Pat. Nos. 5,504, 247 (Sulzer) and 5,831,124 (BASF) and 6,482,981 (Nippon Shokubai), some of which target the purification of acrylic acid synthesized by oxidation of propylene.

The most widely used technique is falling film fractional crystallization, dynamic crystallization, optionally in combination with a static crystallization in a molten medium.

The falling film crystallization is generally carried out in a tubular exchanger, in practise multitubular, each tube being fed continuously (at the top) with:
- a liquid stream (solution or melt) of the compound to be purified, acrylic acid (AA) in the process, falling as a film preferably along the internal wall of the tube, received at the tube bottom and recycled at the top (closed loop) for the time necessary for the crystallization of the amount of compound (AA) decided upon by the operator,
- a stream of heat-exchange fluid, for example ethylene glycol/water or methanol/water, falling as a film, preferably along the external wall of the tube, also recirculated throughout the crystallization within the tube, which will contribute the cold or the heat necessary for the operation of the stages of each of the steps.

The process is a combination of successive steps which each comprise three stages:
- Crystallization: the temperature of the heat-exchange fluid is lowered along a negative temperature gradient starting from a temperature slightly above the crystallization temperature of the acrylic acid in the medium, of the order of 14° C. Crystals form as a more or less thick layer at the surface of the tubes. When approximately 30 to 80% of AA circulated has crystallized, after draining, the remaining liquid fraction (mother liquors rich in impurities) is transferred into a receiver.
- Sweating: the temperature of the heat-exchange fluid is raised along a positive temperature gradient in order to remove, by melting, the impurities trapped in the form of inclusions in the layer of acrylic acid crystals being formed; the latter are mainly located in the outermost layer which is in contact with the recirculated stream increasingly rich in impurities. During the sweating, the first molecules to melt are eutectic mixtures of impurities and of AA (acrylic acid), the impurities located in the layer of crystals migrate towards the outer layer, that is to say that which was in contact with the recirculated stream. A small portion of this crystal layer is thus melted and transferred into a receiver, preferably the same receiver as that of the mother liquors recovered during the crystallization stage. This sweating stage can be replaced by a washing technique, which consists in removing impurities present at the surface by washing with pure AA, preferably introduced at a temperature slightly higher than the melting point of the AA layer. However, this technique is a priori less effective.
- Melting: the temperature of the heat-exchange fluid is rapidly increased above the melting point of AA (14° C.) and should preferably remain below a maximum temperature above which it is possible to fear a polymerization (explosive) of the medium: this maximum temperature is of the order of 35-40° C. in order to remain secure in melting the layer of crystals of purified AA. The purified liquid recovered is placed in a second receiver.

Starting from the stream to be purified, the combined three stages described represent a first purification step. The purified liquid can, on conclusion of this first step, be again subjected to a sequence of the three stages described in a 2nd purification step (purification phase). The mother liquors resulting from this 2nd step are purer than those from the preceding step and can thus be used as a mixture with a fresh charge of AA to be purified in step No. 1. The same operation can be carried out in a third purification step, it being possible for the mother liquors from this third step to be recycled in the charge of the 2nd step and the pure product being recovered by melting the crystals. Generally, the mother liquors from the "n" purification step can be recycled by mixing them with the feed stream of the "n–1" purification step.

During the purification phases, the polymerization inhibitors present in the mixtures to be purified are treated as impurities and are thus removed in the mother liquors. In order to prevent the formation of polymer in the molten crystallizate, an inhibitor compatible in nature and concentration with the final use of the monomer is preferably added. This addition will in particular be carried out during the final melting stage of a step fed with a stream devoid of polymerization inhibitor, such as, for example, the final melting stage purification step fed solely with a purified stream from the "n–1" step.

The mother liquors collected subsequent to the first purification step can be treated in a "–1" step according to the same three-stage process. The crystallizate recovered can be used as supplement for the feed charge of the first step. The mother liquors from the "−1" step are then treated according to the same process for a further separation, the crystallizate of which will participate as charge in the step immediately above and the mother liquors of which are again subjected to the process in a lower "−2" step. The steps "−1", "−2", and the like, constitute the concentration steps (the successive steps make it possible to concentrate the impurities in the mother liquor streams). Generally, the mother liquors from the "n" concentration steps are treated according to the same three-stage process in the subsequent "n−1" step. The repetition of these operations (concentration phase) will make it possible to concentrate the impurities in a stream of mother liquors increasingly rich in impurities, while the fractions of pure acrylic acid will be returned to the initial step. Thus, it is possible to recover the acrylic acid entrained in the initial mother liquors in order to improve the recovery yield and furthermore to obtain a mixture "enriched" in impurities and in propionic acid.

The successive concentration steps are characterized by streams of mother liquors increasingly concentrated in impurities and in propionic acid as these steps accumulate. In doing this, the crystallization temperature of these mixtures becomes increasingly low, which has the effect of increasing the energy cost of cooling. Furthermore, the time necessary to crystallize the same amount of acrylic acid is increasingly long, which has the consequence of reducing the productive output of the purification for the same crystallization surface area. Consequently, the number of the concentration steps will generally preferably be halted before the total concentration of the impurities and of propionic acid in the mother liquors exceeds 50% by weight of the stream.

Depending on the purity of the starting material, the purity of the expected purified product and the recovery yield desired, the complete process for an initial AA quality of "technical" type preferably comprises from 1 to 5 steps of purification of acrylic acid and from 1 to steps for the concentration of the impurities and of the propionic acid, more preferably from 1 to 4 steps of purification and from 1 to 4 steps for the concentration of the impurities and of the propionic acid. This is an advantage for the process according to the invention as these purification and concentration steps require the consumption of a great deal of energy; a limited number of steps makes it possible to obtain a more economical process while obtaining a good yield of propionic acid.

In order to further improve the recovery yield, it is also possible to carry out the final concentration step in a static crystallizer. In this case, the mixture to be crystallized is placed in contact with a cooled wall. It can, for example, be an exchanger composed of metal plates through which a heat-exchange fluid circulates and which are immersed in a vessel containing the crystallization mother liquors from the preceding steps. The AA forms a crystal layer on the walls of the plates and the mother liquors concentrated in propionic acid and in impurities are recovered.

During the process according to the invention, at least one stream of mother liquors, preferably the stream of mother liquors from the final concentration step, is isolated.

According to the invention, the stream of mother liquors isolated during the fractional crystallization is hydrogenated in the presence of molecular hydrogen in order to obtain propionic acid.

The stream of mother liquors preferably comprises from 50 to 90% by weight of acrylic acid.

This hydrogenation can be carried out in the liquid phase or in the gas phase.

For example, the hydrogenation can be carried out:

by homogeneous liquid-phase catalysis, it being possible for the catalyst to be a ruthenium-phosphine complex and the solvent being methanol, at a temperature of approximately 60° C. and at a pressure of approximately 3 MPa;

by heterogeneous gas-phase catalysis over a hydrogenation catalyst, for example copper/zinc deposited on an aluminum oxide; the reaction is then carried out in a fixed bed at a temperature between 250° C. and 350° C. and at a pressure of between 1 atm and approximately 6 atm;

by heterogeneous catalysis over a palladium catalyst applied in the form of a liquid palladium salt solution absorbed on a porous support, such as silicic acid or an active charcoal, the salt subsequently being reduced to form metallic palladium. An advantage of this process is that it can be carried out under "mild" conditions, that is to say at temperatures of 20 to 80° C. and hydrogen pressures of 1 to 10 atm, which makes it possible to limit polymerization reactions of the acrylic acid.

This process is described in detail on pages 2 to 4 of the document FR 2 219 927, the content of which is incorporated by reference.

Mention may also be made of the documents Chem. Prum., 37 (1987), pp. 651 to 653, and Electroanalytical Chemistry, (1975), pp. 75 to 80, which describe other processes for the hydrogenation of acrylic acid to give propionic acid.

Preferably, the hydrogenation is carried out in the gas phase: according to this alternative form, the hydrogenation catalyst is subjected to less interference from the possible presence of polymerization inhibitors.

In the liquid phase, in the case where a sulfur-comprising polymerization inhibitor was used during the preceding stages of separation by distillation, it is preferable to carry out, before hydrogenation, a stage of prior purification of the mother liquors, for example by distillation, a sulfur-free polymerization inhibitor optionally being added during this purification. It is also possible to use a "capturing body" before hydrogenation, that is to say to place solid compounds capable of scavenging sulfur-comprising inhibitors, such as ZnO, $Ti_xCe_yO_2$, such as described in the application US 2009/065400, and/or supported metals, such as Mo and/or Ni and/or Co, in the oxide or sulfide form, before introducing the hydrogenation catalyst or upstream of the latter.

The propionic acid solution resulting from hydrogenation reaction comprises impurities, such as acetic acid, which can be easily separated by an additional stage of purification by distillation.

At the end of the process, a bioresourced propionic acid composition is obtained having as object a bioresourced propionic acid composition having a concentration of propionic acid of greater than 85% by weight, preferably of greater than 95% by weight and more preferably of greater than 99% by weight.

The invention also relates to the use of said bioresourcedd propionic acid composition or of the bioresourcedd propionic acid obtained according to the process of the invention as solvent, as food preservative or in herbicide manufacture, in the preparation of perpropionic acid or in the preparation of vinyl propionate, which is used as monomer in (co)polymers.

The application of a stage of fractional crystallization of the acrylic acid combined with the hydrogenation of the mother liquors isolated at the end of this stage exhibits the advantage of fully achieving the objectives desired in the present patent application, that is to say to obtain a bioresourced propionic acid and to limit the losses of product during the manufacture of a purified acrylic acid using an ex-glycerol process.

The process for the manufacture of propionic acid according to the invention is illustrated by the following examples.

EXAMPLE 1

Manufacture of Crude Acrylic Acid from Glycerol

The preliminary stage consists in purifying the crude glycerol obtained from vegetable oil, the salts being removed. The crude glycerol solution consists, by weight, of 89.7% of glycerol, 3.9% of water and 5.1% of sodium chloride. This stream (6400 g) is continuously conveyed as feed to a stirred 2 liter reactor heated by an external electrical reactor heater. The glycerol and water vapors are condensed in a reflux condenser and recovered in a receiver. This purification operation is carried out under a pressure of 670 Pa (5 mmHg). 5710 g of a glycerol solution devoid of sodium chloride are obtained.

Passing to stage (1) of the process, the reaction for the dehydration of the glycerol to give acrolein and the condensation (1') of a portion of the water are carried out. The dehydration reaction is carried out in the gas phase in a fixed bed reactor in the presence of a solid catalyst consisting of a tungstated zirconia $ZrO_2/WO_3$ at a temperature of 320° C. at atmospheric pressure. A mixture of glycerol (20% by weight) and water (80% by weight) is conveyed to an evaporator in the presence of air in an $O_2$/glycerol molar ratio of 0.6/1. The gas medium exiting from the evaporator at 290° C. is introduced into the reactor, consisting of a tube with a diameter of 30 mm charged with 390 ml of catalyst and immersed in a salt bath ($KNO_2$, $NaNO_3$ and $NaNO_2$ eutectic mixture) maintained at a temperature of 320° C.

At the outlet of the reactor, the gaseous reaction mixture is conveyed to the bottom of a condensation column. This column consists of a lower section filled with Raschig rings surmounted by a condenser in which a cold heat-exchange fluid circulates. The cooling temperature in the exchangers is adjusted so as to obtain, at the column top, a temperature of the vapors of 72° C. at atmospheric pressure. Under these conditions, the loss of acrolein at the condensation column bottom is less than 5%.

In the following stage (2), the gas mixture is introduced, after addition of air ($O_2$/acrolein molar ratio of 0.8/1) and of nitrogen in an amount necessary in order to obtain an acrolein concentration of 6.5 mol %, as feed of the reactor for the oxidation of acrolein to give acrylic acid. This oxidation reactor consists of a tube with a diameter of 30 mm charged with 480 ml of a commercial catalyst for the oxidation of acrolein to give acrylic acid based on mixed oxides of aluminum, molybdenum, silicon, vanadium and copper and immersed in a salt bath, identical to that described above, for its part maintained at a temperature of 345° C. Before introducing over the catalytic bed, the gas mixture is preheated in a tube which is also immersed in the salt bath.

At the outlet of the oxidation reactor, the gas mixture is introduced at the bottom of an absorption column, stage (3), operating at atmospheric pressure. This column is filled with random packing made of stainless steel of ProPak type. In the lower part, over 1/3 of its total height, the column is equipped with a condensation section; a portion of the condensed mixture recovered at the column bottom is recycled, after cooling in an external exchanger, at the top of this condensation section. The upper part of the column is cooled by exchange of heat through the wall. The temperature of the vapors at the column top is 25° C. and that of the aqueous solution of crude acrylic acid obtained at the column bottom is 35° C. The product obtained at the bottom (crude acrylic acid) comprises 40% of water and a mixture of acrylic acid (predominant product) and of impurities, present in "impurities/AA" ratios by weight shown in table 1 below. An aqueous hydroquinone (HQ) solution is introduced continuously into the recirculation loop at the column bottom at a concentration of 0.1% by weight, with respect to the acrylic acid.

EXAMPLE 2

Purification of the Crude AA Obtained Ex-glycerol to Give Technical AA

The aqueous solution obtained is subjected to a stage (4) of drying by distillation in order to remove the water in the form of an azeotropic mixture with methyl isobutyl ketone (MIBK). The column, packed with ProPak elements representing an efficiency of 15 theoretical plates, is fed at its middle with crude AA and at the top with MIBK in an MIBK/water present in the crude AA ratio by weight of 3/1. A solution of stabilizers in MIBK is injected continuously at the column top, which solution comprises the stabilizers hydroquinone, phenothiazine and butyl dibutyldithiocarbamate (respectively: 35 ppm, 70 ppm and 35 ppm, with respect to the acrylic acid present in the feed stream). The azeotropic mixture distills at a top temperature of 45° C. under a pressure of $1.2 \times 10^4$ Pa.

The dehydrated acrylic acid recovered at the column bottom comprises no more than 0.4% of water.

It is sent, stage (5), as feed of a topping column, which makes it possible to remove the light compounds, essentially acetic acid, at the top. This column, packed with ProPak elements (20 theoretical plates) is fed at its middle with the stream of dehydrated AA and a stream rich in acetic acid is distilled at the top under a pressure of $1.3 \times 10^4$ Pa at a top temperature of 77° C. with a reflux ratio of 7/1. A solution of stabilizers in technical acrylic acid comprising the stabilizers hydroquinone and butyl dibutyldithiocarbamate (400 ppm, with respect to the acrylic acid present in the feed stream) is introduced at the distillation column top. The yield for recovery of the acrylic acid in this stage is 97%.

The topped acrylic acid recovered at the bottom of this column has an acetic acid content of 0.07%. It is conveyed, stage (6), as feed of a tailing column provided with 17 perforated plates comprising weirs which makes it possible to remove the heavy compounds at the bottom. This column operates under a pressure of $6.7 \times 10^3$ Pa with a top temperature of 73° C. and with a reflux of 0.5/1. A solution of stabilizers in technical acrylic acid, comprising the stabilizers phenothiazine and butyl dibutyldithiocarbamate (400 ppm, with respect to the acrylic acid present in the feed stream), is introduced at the top plate of the distillation column and the condensed distillate stream is additivated with a solution of hydroquinone in pure AA (200 ppm, with respect to the distilled acrylic acid). The acrylic acid obtained at the column top constitutes the technical acrylic acid (TAA).

The analyses of the technical grade acrylic acid show that the product comprises 0.07% of acetic acid, 0.66% of propionic acid, 0.11% of maleic anhydride, 0.11% of water, 0.023% of 2-butenoic acid, 0.01% of furfural, 0.02% of benzaldehyde, 0.01% of protoanemonin and 0.02% of acrolein.

The yield for recovery of the acrylic acid in this stage is 95.5%.

EXAMPLE 3

Manufacture of Propionic Acid from Ex-glycerol Technical Acrylic Acid Purified by Crystallization (1)

The stream of acrylic acid of technical quality obtained in example 2 is subjected to a series of purification and concentration steps by fractional crystallization, as described in the present application. The arrangement used is a falling film crystallizer consisting of a vertical tube made of stainless steel filled with heat-exchange fluid (ethylene glycol/water mixture) circulating in a closed circuit, via a pump, through an external heat exchanger which can be programmed as a temperature gradient (Lauda cryostatic bath). This tube is fed at the top in the form of a liquid film which flows uniformly over its external wall. The liquid constituting the mixture to be crystallized, recovered in a receiving tank at the bottom, recirculates as a loop in a lagged circuit in order to again feed the tube at the top, via a pump.

The stream of technical acrylic acid is subjected to a series of several successive purification steps, each step comprising the following stages:

Crystallization: the heat-exchange fluid is rapidly cooled, so as to lower the temperature of the falling film of acrylic acid down to the temperature of crystallization of the acrylic acid in the mixture, determined beforehand from a sample of the mixture to be purified, and then a negative temperature gradient, of 0.1 to 0.5° C./min, is imposed on the heat-exchange fluid. When the volume of crystallized acrylic acid, measured by difference by evaluating the level of liquid in the collecting container at the bottom of the crystallizer, reaches 70% of the starting mixture, the recirculation of the falling film of mixture to be purified is halted and the tube is drained. The liquid mixture of the mother liquors thus obtained is separated and stored in a receiver.

Sweating: the heat-exchange fluid is reheated, so as to bring about the melting of a portion (5%) of the layer of crystallized acrylic acid at the surface of the tube. The mother liquors from this sweating stage are collected and stored in the same receiver as the mother liquors from the preceding stage.

Melting: the heat-exchange fluid is rapidly reheated up to a temperature of 30° C., until the crystallized layer has completely melted. The purified liquid stream is placed in a different receiver.

The product purified by melting in the final stage of the first purification step is conveyed to the second purification step, where it will be subject to a fresh series of the three purification stages under the same operating conditions. The mother liquors from the second purification step are subsequently mixed with a fresh charge of the feed stream of technical AA in step 1. This process is thus repeated until the desired quality is obtained in the molten purified product.

In order to limit the losses of acrylic acid which are concentrated in the mother liquors from a first purification step, a series of successive concentration steps, exhibiting the same stages as the purification steps, is carried out in which the crystallizate from the "n−1" step is conveyed as feed of the "n" step and the mother liquors from this "n−1" step are conveyed as feed of the "n−2" step. These steps are carried out under the same operating conditions as the purification steps, except for the volume of crystallized acrylic acid targeted, before passing from the crystallization stage to the sweating stage, which is 60% of the product fed.

The final crystallization step is carried out in static mode. The stream to be purified is placed in a container made of stainless steel with a jacket through which circulates a cold fluid maintained at the crystallization temperature of the medium, determined beforehand by a measurement of crystallization temperature. A vertical tube made of stainless steel filled with heat-exchange fluid (ethylene glycol/water mixture) circulating in a closed circuit, via a pump, through an external heat exchanger which can be programmed as a temperature gradient is immersed in this container.

In a first stage, the temperature of the heat-exchange fluid in the tube is rapidly lowered to the crystallization temperature of the medium and then a negative temperature gradient of 0.1 to 0.5° C./min is imposed. When the crystallized volume reaches approximately 50% of the starting product, the mother liquors are removed, a sweating stage is then carried out and, finally, the melting stage is carried out, as in the upper crystallization steps in dynamic mode.

Applied to the technical acrylic acid obtained from glycerol on completion of the purification stages of example 2, a sequence of 4 purification steps and 3 concentration steps, including a crystallization step in static mode, made it possible to obtain acrylic acid of "glacial" quality comprising 50 ppm of acetic acid, 410 ppm of propionic acid, less than 1 ppm of maleic anhydride, less than 80 ppm of water, less than 1 ppm of 2-butenoic acid, less than 1 ppm of furfural, less than 1 ppm of benzaldehyde, less than 1 ppm of protoanemonin and less than 1 ppm of acrolein.

The yield for recovery of AA in this purification stage is 96.5%.

The residual mother liquors from the final concentration step have the following composition:
Acrylic acid: 82.4% by weight
Acetic acid: 1.7% by weight
Propionic acid: 7.4% by weight
Diacrylic acid: 0.6% by weight
Furfurals: 0.3% by weight
Benzaldehyde: 0.6% by weight
Water: 2.5% by weight
Hydroquinone: 0.5% by weight Manufacture of the Propionic Acid Solution A jacketed tubular evaporator made of stainless steel (length of the tube 100 cm, internal diameter 2.5 cm, wall thickness 4 mm) was packed over its entire length with Raschig rings made of silica.

A jacketed tubular reactor made of stainless steel identical to the evaporator was packed, from the bottom upwards, first over a length of 5 cm with Raschig rings and then the jacketed tubular reactor was packed with a homogeneous mixture of 130 ml=135.1 g of the Johnson Matthey hydrogenation catalyst of 50B type (0.3% by weight of Pd on $\gamma$-$Al_2O_3$, as 2 mm spheres) and of 226 ml of Raschig rings. The remainder of the length of the jacketed tubular reactor was packed only with Raschig rings.

The intermediate space both of the jacketed tubular evaporator and of the jacketed tubular reactor was provided with an oil forming a heat-exchange fluid which exhibits a temperature of 185° C.

10 g/h of the residual mother liquors were introduced (from the top downwards) into the jacketed tubular evaporator. 16 mol/h of molecular hydrogen were passed through the tubular evaporator countercurrentwise to these mother liquors.

The mixture of acrylic acid and of molecular hydrogen exiting from the evaporator was immediately conveyed, from the bottom upwards, through the jacketed tubular reactor. The end of the latter is at atmospheric pressure. The temperature in the middle of the reactor is approximately 220° C. The unreacted acrylic acid and the propionic acid produced were recovered by condensation in a separator at 10° C.

After an operating time of 100 h, the condensate comprised 813 g of propionic acid.

After distillation, a propionic acid solution having a purity of 99.1% is recovered.

EXAMPLE 4

Manufacture of Propionic Acid from Ex-glycerol Technical Acrylic Acid Purified by Crystallization (2)

The same purification of the ex-glycerol technical AA by crystallization is carried out as in the preceding example, except that an additional concentration step in dynamic mode is carried out, e.g. 4 purification steps and 4 concentration steps, including one in static mode.

The yield for recovery of AA in this purification stage is 99.3%.

The mother liquors recovered after the final concentration stage have the following composition:
54.4% of acrylic acid,
7.3% of water,
8.9% of maleic anhydride,
4.4% of acetic acid,
16.7% of propionic acid,
and 1.5% of hydroquinone.
Manufacture of the Propionic Acid Solution In this instance, the hydrogenation is carried out in the liquid phase with a Pd/C catalyst.

200 g of solution of the mother liquors, 200 g of propionic acid already recovered, simulating a process with recycling, and 50 g of Johnson Matthey catalyst of 87 G type are added with magnetic stirring at 60° C. to an autoclave and then the combined mixture is reacted with hydrogen under an absolute pressure of 7 bar for 2 hours. After reaction, 340 g of propionic acid are recovered.

EXAMPLE 5

Manufacture of Propionic Acid from Ex-glycerol Topped Acrylic Acid Purified by Crystallization The same treatment series as in example 3 (with a static crystallization step) are applied to the stream obtained at the bottom of the topping column (stage (5) of example 2).

A series of 4 purification steps and 3 concentration steps, including a static crystallization step, made it possible to obtain acrylic acid of "glacial" quality comprising less than 50 ppm of acetic acid, 500 ppm of propionic acid, less than 1 ppm of maleic anhydride, less than 100 ppm of water, less than 1 ppm of 2-butenoic acid, less than 1 ppm of furfural, less than 1 ppm of benzaldehyde, less than 1 ppm of protoanemonin and less than 1 ppm of acrolein.

The residual mother liquors from the final concentration step have the following composition:
Acrylic acid: 67% by weight
Acetic acid: 1.6% by weight
Water: 2.3% by weight
Maleic anhydride: 9.4% by weight
Propionic acid: 7.4% by weight
Furfurals: 0.3% by weight, and
Hydroquinone: 0.8% by weight.
Manufacture of the Propionic Acid Solution A jacketed tubular evaporator made of stainless steel (length of tube 85 cm, internal diameter 3 cm, wall thickness 4 mm) was packed over its entire length with Raschig rings (material $SiO_2$, quartz glass; external diameter 3 mm, internal diameter 2 mm, length 3 mm).

A jacketed tubular reactor made of stainless steel (length of the tube 120 cm, internal diameter 3 cm, wall thickness 4 mm) was packed over its entire length with a homogeneous mixture of 400 ml=446 g of the Johnson Matthey hydrogenation catalyst of 48 type (0.5% by weight of Pd on $\gamma$-$Al_2O_3$, extrudates as 3 mm pellets) and of 400 ml of Raschig rings. The intermediate space both of the jacketed tubular evaporator and of the jacketed tubular reactor was filled with an oil forming a heat-exchange fluid. The oil forming a heat-exchange fluid of the evaporator had a temperature of 210° C. and that of the reactor had a temperature of 180° C.

10 g/h of the residual mother liquors were introduced (from the top downwards) into the jacketed tubular evaporator. 50 mol/h of molecular hydrogen were passed through the jacketed tubular evaporator countercurrentwise to the acrylic acid.

The mixture of acrylic acid and of molecular hydrogen exiting from the evaporator was immediately conveyed from the bottom upwards through the jacketed tubular reactor positioned above the evaporator. The end of the tube is at atmospheric pressure. The temperature in the middle of the reactor is 186° C. The unreacted acrylic acid present in the gas stream produced and the propionic acid formed are separated by condensation in a separator at 10° C.

After an operating time of 20 h, 13.2 g of propionic acid are recovered in the condensate.

The propionic acid produced according to the invention is a bioresourced acid manufactured from nonfossil natural starting materials.

What is claimed is:

1. A process for the manufacture of bioresourced propionic acid from glycerol comprising the following stages:
    dehydrating, in the gas phase, glycerol to an acrolein containing mixture, in the presence of a first catalyst, (1)
    partially condensing, by cooling, the acrolein containing mixture and extracting water present in the acrolein containing mixture to give acrolein, (1')
    oxidizing, in the gas phase in the presence of a second catalyst, the acrolein to give an acrylic acid stream, (2)
    extracting an acrylic acid solution from the acrylic acid stream by absorption with a solvent, (3)
    drying the acrylic acid solution by distillation in the presence of a water-immiscible solvent to form a dry acrylic acid heavy solution, (4)
    distilling the dry acrylic acid heavy solution in a distillation column to remove light compounds at the top of the distillation column and a heavy fraction at the bottom of the distillation column, (5)
    distilling the heavy fraction resulting from the preceding stage (5) to remove heavy compounds to give a light fraction, (6)
    the process further comprising:
    extracting acrylic acid by fractional crystallization from one or more of:
        the dry acrylic acid heavy solution from (4),
        the heavy fraction from (5)
        or light fraction from (6),
    in order to isolate crystals of purified acrylic acid and a solution of mother liquors depleted in acrylic acid;
    catalytic hydrogenation of the mother liquors isolated in the fractional crystallization stage in the presence of molecular hydrogen in order to form a propionic acid solution; and separation of the propionic acid from the propionic acid solution.

2. The process as claimed in claim 1, further characterized in that a liquid fraction resulting from (3) is subjected to a separation (3') of residual acrolein by distillation or stripping with a gas.

3. The process as claimed in claim 1, further characterized in that a heavy fraction from (4) is subjected to a stage of extraction of acrylic acid by fractional crystallization.

4. The process as claimed in claim 1, further characterized in that the heavy fraction from (5) is subjected to a stage of extraction of acrylic acid by fractional crystallization.

5. The process as claimed in claim 1, further characterized in that the light fraction from (6) is subjected to the stage of extraction of acrylic acid by fractional crystallization.

6. The process as claimed in, claim 1 in which the catalytic hydrogenation is carried out in the gas phase.

7. The process as claimed in, claim 1, further comprising adding a sulfur-free polymerization inhibitor during one or more of the distillation stages.

8. The process as claimed in, claim 1, in which the fractional crystallization comprises from 1 to 5 steps of purification of acrylic acid and from 1 to 5 steps of concentration of impurities and of propionic acid.

9. The process as claimed in claim 1, wherein the separation of the propionic acid from the propionic acid solution is by distillation.

* * * * *